US008586335B2

(12) United States Patent
Bell et al.

(10) Patent No.: US 8,586,335 B2
(45) Date of Patent: *Nov. 19, 2013

(54) PROCESS FOR THE PRODUCTION OF ETHANOL AND BUTANOL

(75) Inventors: Peter Simpson Bell, Fayetteville, AR (US); Stephen John Benstead, Callander (GB); Neil Turnbull, Dalgerty Bay (GB)

(73) Assignee: INEOS Bio SA, Lisle, IL (US)

( * ) Notice: Subject to any disclaimer, the term of this patent is extended or adjusted under 35 U.S.C. 154(b) by 81 days.

This patent is subject to a terminal disclaimer.

(21) Appl. No.: 12/736,101

(22) PCT Filed: Feb. 19, 2009

(86) PCT No.: PCT/EP2009/051966
§ 371 (c)(1),
(2), (4) Date: Nov. 1, 2011

(87) PCT Pub. No.: WO2009/112335
PCT Pub. Date: Sep. 17, 2009

(65) Prior Publication Data
US 2012/0040427 A1    Feb. 16, 2012

(30) Foreign Application Priority Data

Mar. 11, 2008 (EP) .................................... 08102478
May 19, 2008 (GB) .................................... 0809019.3

(51) Int. Cl.
*C12P 7/40* (2006.01)
(52) U.S. Cl.
USPC ........................................................ 435/136

(58) Field of Classification Search
USPC ............................................................ 435/136
See application file for complete search history.

(56) References Cited

U.S. PATENT DOCUMENTS 5,753,474 A * 5/1998 Ramey .......................... 435/136
2003/0211585 A1   11/2003 Gaddy
2007/0275447 A1   11/2007 Lewis

FOREIGN PATENT DOCUMENTS

WO   WO 2006/119052   11/2006
WO   WO 2008/115080   9/2008
WO   WO 2009/112335   9/2009

* cited by examiner

*Primary Examiner* — Maryam Monshipouri
(74) *Attorney, Agent, or Firm* — Vikrant B. Panchal; INEOS Bio SA

(57) ABSTRACT

The present invention relates to a process for the production of ethanol and butanol from biomass, and in particular to a process for the production of ethanol and butanol using two separate fermentation steps, said process comprising: a) passing a biomass feedstock to a first fermentation step, b) in said first fermentation step subjecting the biomass feedstock to anaerobic fermentation at a pH below 6.0 and at a temperature in the range 20 to 700° C. and so as to convert the biomass to a product predominantly comprising acetic acid and butyric acid with at least a 2:1 ratio by weight of acetic acid to butyric acid, c) treating the product stream of step (b) to separate a solution comprising the acetic acid and butyric acid by: (i) separating a solution comprising the acetic acid and butyric acid from any residual solids and (ii) separating bacteria and/or pasteurising or sterilising the solution from the first fermentation step, and d) in a second fermentation step fermenting the solution comprising the acetic acid and butyric acid from step (c) to form ethanol and butanol.

14 Claims, No Drawings

PROCESS FOR THE PRODUCTION OF ETHANOL AND BUTANOL

This application is a 371 of PCT/EP2009/051966, filed Feb. 19, 2009, which claims foreign priority to European application No. 08102478.8, filed Mar. 11, 2008, and British application No. 0809019.3, filed May 19, 2008.

The present invention relates to a process for the production of ethanol and butanol from biomass, and in particular to a process for the production of ethanol and butanol using two separate fermentation steps.

It has been known for many years that bacteria cause the anaerobic fermentation or digestion of biomass resulting in various gases which can be utilised. As early as the late 19$^{th}$ Century the products of anaerobic digestion were used to generate methane gas for use in street lighting. More recently, anaerobic fermentation has been considered as both a means to reduce the amount of organic matter which is sent to landfill and as an alternative method for production of useful chemicals, such as alcohols.

For example, U.S. Pat. No. 5,753,474 describes a continuous two-stage anaerobic fermentation process to produce butanol using two different strains of bacteria.

The process of U.S. Pat. No. 5,753,474 uses specific strains of bacteria in each stage, and it is necessary to pre-treat the biomass feedstock to sterilise it and kill background bacteria, and thus ensure that the desired bacteria in the first stage can flourish. In such a process the use of a specific strain in the first stage is necessary to obtain high selectivity to a product, such as butyric acid, which is not a "complete" fermentation product. By this it meant that, without the use of a specific selective bacteria as in U.S. Pat. No. 5,753,474, the butyric acid is broken down further to lower acids. In such a process it is also relatively complicated to keep the bacteria alive, which means such processes need significant technical expertise. As an example, it is known that bacteria can be sensitive to butanol inhibition, even to the extent of death of the bacteria being caused by the butanol product. Thus, U.S. Pat. No. 5,753,474 itself notes that it is necessary to keep the product solvents concentration in the solventogenesis reactor below 1.0 wt % to prevent inhibition or even death of the bacteria. However, at such low concentrations it is not economically viable to separate the produced butanol.

For example, in the Encyclopedia of Bioprocess Technology—Fermentation, Biocatalysis, and Bioseparation, Volumes 1-5, p. 670-687 the use of *clostridium* to solventogenise organic acids to the corresponding alcohols is discussed, but it is stated on p. 684 that "It has been calculated that when distillation is used in the recovery of ethanol at less than 6-8%, or n-butanol at less than 2 to 3% from fermentation beers, the energy requirement exceeds the net energy recovery in the final products obtained in the commercial process."

We have now found that a significant improvement can be obtained when producing both ethanol and butanol, with ethanol as the desired predominant final product. In such a case a significant amount of the complexity in the first fermentation step can be avoided because it is not necessary to prevent butyric acid conversion to acetic acid. In fact, such a conversion is desired to ensure that the majority the product acid is acetic acid. The particular advantages of this are that no specific individual bacterial strain is required.

Further, it has been found that the inhibition by product ethanol of the bacteria in the subsequent solventogenesis reaction is not as strong as inhibition by butanol. Therefore, although the concentration of both products should be controlled below certain limits, the total concentration of solvents in the product stream can be significantly higher than is taught by U.S. Pat. No. 5,753,474. This has been found to have significant advantages in allowing economical separation.

Thus, in a first aspect the present invention provides a process for the production of ethanol and butanol using two separate fermentation steps, said process comprising:
  a) passing a biomass feedstock to a first fermentation step,
  b) in said first fermentation step subjecting the biomass feedstock to anaerobic fermentation at a pH below 6.0 and at a temperature in the range 20 to 70° C. and so as to convert the biomass to a product predominantly comprising acetic acid and butyric acid, and with at least a 2:1 ratio by weight of acetic acid to butyric acid,
  c) treating the product stream of step (b) to separate a solution comprising the acetic acid and butyric acid by:
    (i) separating a solution comprising the acetic acid and butyric acid from any residual solids and
    (ii) separating bacteria and/or pasteurising or sterilising the solution from the first fermentation step,
  and
  d) in a second fermentation step fermenting the solution comprising the acetic acid and butyric acid from step (c) to form ethanol and butanol.

The biomass feedstock in step (a) may be any suitable biomass feedstock including, but not limited to, municipal solid waste, lignocellulosic biomass, landfill leachate, carbohydrates, fats and proteins. Specific examples are the biodegradable portion of municipal and industrial wastes, biosludge, energy crops and agricultural residues.

The feedstock may be treated by conventional means, such as milling, to make it more easily digested in step (b). However, whilst such a step is not precluded, the feedstock need not be pasteurised or sterilised to remove bacteria therefrom in the process of the present invention. In fact, the use of the bacteria inherently present in the biomass in the first fermentation step can be an advantageous feature of the present invention, and thus step (a) preferably comprises passing a biomass feedstock without pasteurisation or sterilisation to the first fermentation step.

As used herein, "sterilise" means to treat to effectively kill all bacteria therein. This is typically achieved by application of heat, although other means, such as irradiation, are also known.

As used herein, "pasteurise" means to treat for the purpose of killing bacteria to achieve a 5-log reduction (0.00001 times the original) in the number of live bacteria. Thus, pasteurisation can be distinguished from sterilisation in that some bacteria survive the process. Pasteurisation is typically also performed by the application of heat, generally at lower temperature and/or for a shorter period of time than a corresponding sterilisation. Again, other means, such as irradiation, are also known.

The feedstock pre-treatment is generally selected dependent on the specific feedstock and as necessary or advantageous to make the feedstock more suitable for fermentation. Typically this involves methods to effect size reduction in order to provide improved access for the bacteria and improve the rate of conversion. Examples of known techniques are shredding, milling, ultrasound, hydrocrushing, steam explosion.

In step (b) the biomass feedstock is subjected to anaerobic fermentation at conditions to convert the biomass to a product predominantly comprising acetic acid and butyric acid. The fermentation takes place using a mixture of bacterial strains, which mixture may include bacterial strains present in the biomass feedstock (when pasteurisation or sterilisation of the feedstock is not performed). In fact, a particular advantage of the process of the present invention is that it can be applied widely to different types of biomass by using a mixture of bacterial strains.

There are four key stages in normal anaerobic digestion: hydrolysis, acidogenesis, acetogenesis and methanogenesis. Through hydrolysis, complex organic molecules are broken down into simple sugars, acids and amino acids. Bacteria convert these molecules to volatile fatty acids through the process of acidogenesis. In the third stage, acetogenesis of the volatile fatty acids occurs and they are converted to carboxylic acids, such as acetic acid and butyric acid. The final stage in normal anaerobic digestion is methanogenesis, in which acetic acid is broken down to form methane and carbon dioxide.

Generally, the bacteria present in anaerobic digestion can be classified by the final product as either acetogens or methanogens. Both types are likely to be present in the biomass feedstock and in step (b) of the present invention.

In general, in a fermentation process in which a mixture of bacterial strains are present, certain bacteria will "thrive", whilst others will not. The bacteria which will thrive will be those that can grow under the conditions of the fermentation. Other bacteria may survive (but be "inhibited") or may die. In any such fermentation it may be difficult to determine the exact mixture of bacterial strains present, and populations of certain bacteria may vary significantly with what may otherwise seem minor changes in fermentation conditions. Nevertheless, by selection of conditions which have been found to favour the production of the desired product(s), bacteria which produce such product(s) will be selectively maintained in the reactor. The use of a mixture of bacterial strains present in the first fermentation step will also enable the bacterial populations to adjust (or "evolve") when the feedstock is changed to favour those which thrive on the particular feedstock. Processes in which mixtures of bacteria are utilised to produce particularly desired products are described, for example, in US 2003/211585 and US 2006/024801.

In the process of the present invention, the conditions in the first fermentation step are maintained to favour a product predominantly comprising acetic acid and butyric acid, which effectively means conditions that inhibit the methanogenic bacteria, but which allow acetogenic bacteria to thrive. The principal condition necessary for this is the pH, and in the process of the present invention the pH is maintained below 6.0, preferably at a pH in the range 3 to 5.5. At this pH the methanogenic bacteria are inhibited in their activity and reproduction. Generally, acetogenic bacteria also prefer higher temperatures than methanogenic bacteria. Therefore, whilst temperatures in the range 20 to 70° C. may be utilised, preferably the temperature in the first fermentation step is in the range 40 to 60° C., which further inhibits the methanogenic bacteria and favours the acetogenic bacteria.

Under such conditions, acid production is favoured whilst production of methane is inhibited. "Wash out" of the methanogens from the bacterial mass can also occur (the draining of methanogenic bacteria through the outlet of the reactor/digester at a faster rate than their generation). Although "higher" acids such as propionic and butyric acids are also produced by digestion of the biomass, these can be further broken down to acetic acid. In contrast, acetic acid is not broken down further e.g. to formic acid and thus, although butyric acid and other "higher" acids are obtained in the present invention they are generally obtained in smaller amounts than the acetic acid. In the process of the present invention, the acetic acid and butyric acid are the predominant products from step (b), by which is meant that these two products are each present in higher concentrations than any other products. The product distribution in the product stream may be controlled by the conditions in the first fermentation step. Preferably the acetic acid and butyric acid are present in a combined concentration of at least 60 wt %, preferably at least 80 wt % of the total weight of carboxylic acids in the product stream. Acetic acid is the most predominant. It should be noted that the acetic acid, butyric acid and other "acids" produced may not actually all be present in the fermentation broth solely in the form of the acid, but, for example, may be present as acetate or other related compounds, which are only formally converted to acetic acid if suitably "worked-up" from the fermentation broth. Nevertheless, it is customary in the art of fermentation to use the term "acids" to refer to all such compounds, and the yields thereof, even if they are not in the free acid form in the fermentation broth. For avoidance of any doubt, as used herein, general reference to acetic acid, butyric acid or other acids in a fermentation broth includes salts, complexed and chelated compounds thereof, as well as the free acids themselves.

It has also been found that temperature can be used to control the relative amounts of various acids formed in step (b). In particular, temperatures in the range of 50 to 60° C. significantly increase the production of acetic acid over butyric acid and other "higher" acids even compared to lower temperatures in the preferred range of 40 to 60° C., and are thus even more preferred. Under such conditions, the product stream may comprise at least a 4:1 weight ratio of acetic acid to butyric acid and a combined concentration of the acetic acid and butyric acid of at least 90 wt % of the total weight of carboxylic acids in the product stream.

Nutrients may be added to the first fermentation step as and if required. For example, whilst most manures and complex feedstocks usually inherently contain sufficient nutrients for the bacteria in step (b), other feedstocks, such as industrial wastes and crop residues may be deficient. Typical nutrients requirements include nitrogen, phosphorous, magnesium, sodium, manganese, calcium and cobalt. Nutrients are preferably added by mixture of nutrient rich feedstocks, such as manure, with those that may be nutrient-deficient.

An example of a suitable fermentation process for step (a) is bulk fermentation of a biomass pile as described in US 2006/0024801, but any suitable fermentation tank or vessel may also be used. A number of fermentation tanks/vessels are commercially available, such as the Induced Blanket Reactor available from Andigen LC of Ohio, USA.

Compared to the equivalent step in the process of U.S. Pat. No. 5,753,474 the first fermentation step of the present invention is relatively robust, simple to operate and maintain in continuous operation, and flexible to feedstock changes.

Step (b) produces a product solution comprising acetic acid and butyric acid, bacteria and residual solids which can be removed from the first fermentation step. In step (c) this solution is separated to produce a solution comprising the acetic acid and butyric acid. In step (i) a solution comprising the acetic acid and butyric acid is separated from any residual solids. A suitable means of separation for any residual solids is filtration. In step (ii) bacteria from the first fermentation step are separated and/or the solution is pasteurised or sterilised. For example, bacteria may be separated by filtration with a suitably small mesh filter. Alternatively, or in addition to a filtration to remove bacteria, the solution may be pasteurised or sterilised.

For avoidance of doubt, although steps (a) to (d) of the present invention are performed in the sequence presented, steps (i) and (ii) of step (c) may be performed in any suitable order. Thus, the separation of bacteria and/or pasteurisation or sterilisation of the solution from the first fermentation step may be performed prior to the separation of any residual solids.

The resulting solution is passed to step (d) wherein it is fermented in a second fermentation step to form ethanol and butanol.

The fermentation in the second fermentation step uses a solventogenic bacteria. Any suitable solventogenic bacteria may be used. Examples of suitable solventogenic bacteria which may be used in step (d) include *Acetogenium kivui, Acetobacterium woodii, Acetoanaerobium noterae, Clostridium aceticum, Butyribacterium methylotrophicum, Clostridium acetobutylicum, Clostridium thermoaceticum, Eubacterium limosum, Clostridium ljungdahlii, Peptostreptococcus productus, Clostridium carboxydivorans, Clostridium beijerinkii, Clostridium aurantibutyricum,* and *Clostridium tetanomorphum*. Particularly suitable examples are *Clostridium ljungdahlii, Clostridium carboxydivorans, Clostridium acetobutylicum, Clostridium beijerinkii, Clostridium aurantibutyricum,* and *Clostridium tetanomorphum. Clostridium ljungdahlii, Clostridium carboxydivorans* and *Clostridium acetobutylicum* are most preferred.

The solventogenesis process is preferably as described in U.S. Pat. No. 5,753,474.

The ethanol and butanol are obtained from step (d) as a dilute solution in water. Generally, the dilute ethanol and butanol product stream is treated to concentrate and separate the ethanol and butanol with a view to obtaining separate ethanol and butanol streams. The actual final purities of ethanol and butanol desired will depend on the subsequent intended uses, but for ethanol is typically at least 90 wt %, preferably at least 95 wt % and more preferably at least 99 wt %.

The preferred technique for treatment/purification is to use distillation. In a typical distillation column, the butanol may be recovered directly from a side draw on the column. However, ethanol in water cannot be purified by simple distillation to higher than about 95 wt %, at atmospheric pressure, due to the formation of an azeotrope with water. Typically, therefore, the ethanol product is purified to about 90-95 wt % by distillation followed by a drying step, for example on molecular sieve, to give a >99 wt % product. In a preferred embodiment of the present invention, therefore, the initial ethanol and butanol containing product stream from step (d) is treated in a distillation column to produce a butanol containing product stream and an ethanol containing product stream comprising 90 to 95 wt % ethanol, which ethanol containing product stream is subsequently passed to a drying step, especially into contact with a molecular sieve, to remove further water, most preferably to give ethanol in greater than 99 wt % purity.

It is preferable to distil the ethanol to as high a level of purity as possible to reduce the size requirement of the subsequent drying step. However, distilling too close to the azeotrope composition results in an exponential increase in distillation column duty. It is preferable therefore to distil to 94-95 wt % ethanol.

Other alcohols in the product stream may also be removed, as required, by conventional means. Removal from the distillation column as one or more side streams is a preferred example.

The product ethanol and butanol stream from step (d) typically comprises ethanol at a concentration of ethanol in solution of 1 to 5 wt %, more typically in the range 2 to 5 wt %, and butanol at a concentration of butanol in solution of 0.2 to 1 wt %, more typically in the range 0.2 to 0.75 wt %, such as 0.4 to 0.75 wt %.

In particular, when the subsequent treatment/purification comprises distillation, as described above, it is strongly preferred that the initial concentration of ethanol is in the range 2 to 5 wt %. Although such solutions are relatively dilute, it has surprisingly been found that only a small penalty in distillation duty is obtained by using initially relatively dilute feeds. In particular, it has been found that when distilling to high purity the rectification operating line is "pinched" close to the vapour-liquid equilibrium curve near to the azeotrope composition. In contrast, it has been found that the operating line at the bottom end of the vapour-liquid equilibrium curve is not pinched unless the concentration of ethanol in the initial stream is below about 2 wt %. For a higher feed concentration of ethanol the pinch remains at the same point at the top of the curve, and the rectification operating line changes minimally. This means that the reflux ratio, and hence the column duty, does not change significantly as the initial feed composition is increased.

For example, it has surprisingly been found that to produce an overheads stream having 94.5 wt % ethanol by distillation from a feed stream with 20 wt % ethanol saves only just over 10% energy compared to producing a stream of the same concentration from a feed stream with only 4 wt % ethanol.

This is in distinct contrast to what has previously been thought in the art, which was that it was not commercially viable to separate ethanol of high purity from initial streams at such low concentrations by distillation. Thus, as noted previously, in the Encyclopedia of Bioprocess Technology—Fermentation, Biocatalysis, and Bioseparation, Volumes 1-5, p. 670-687 it was stated that it was not viable to separate ethanol at less than 6 to 8%.

The present invention also overcomes the previous problems of economically separating butanol at low concentrations from fermentation broths. Although the butanol concentration in the product stream from step (d) is below 1 wt %, this can be economically recovered because it is recovered in conjunction with ethanol recovery.

More specifically, it has been found that the butanol may be recovered from the distillation column as a side draw. In particular, a stream having a concentration of butanol of about 40 wt % (of the total stream) may be obtained without a significant increase in column duty. Said stream also comprises smaller amounts of propanol and pentanol (collectively known as fusel oils), and quantities of water and ethanol. This stream may be further treated as required. For example, the stream may be treated to separate the respective alcohols, or the alcohols may be used, after water removal, as a mixed alcohols stream.

It is a distinct advantage to be able to separate ethanol and butanol from such dilute streams in step (d) without significant penalty compared to higher concentrations because the concentrations of acetic acid and butyric acid in the product stream removed from step (b) are also relatively dilute. Thus, the product stream from step (b) preferably has a concentration of acetic acid in solution of 1 to 5 wt %, more typically 2 to 5 wt % and a concentration of butyric acid in solution of 0.2 to 1 wt %, more typically in the range 0.2 to 0.75 wt %, such as 0.4 to 0.75 wt %. The concentration of products in said stream can be controlled by the rate at which the product stream is removed from the fermentation.

As noted previously, at higher concentrations of acetic acid or butyric acid, the acids may inhibit formation of further acid, even to the extent that the acids can kill the bacteria. Although the solution removed from step (b) is relatively dilute, an advantage of the present invention is that no concentration is required before the subsequent second fermentation step and any subsequent separations by distillation.

A number of variations and modifications can be made to the overall process of the present invention. In a particular embodiment a portion of the biomass feed to the first fermentation step or a portion of the feed to the second fermentation step is, instead, passed to a third fermentation step where it is anaerobically digested by a methanogenic bacteria to produce methane, which can be used as a fuel gas and used to meet the energy requirements of the overall process, such as distillation and other separations energy requirements. Use of a portion of the feed to the second fermentation step is preferred in this embodiment since this stream has already been "predigested". In addition to meeting the energy requirements of the process, a combined heat and power scheme can be used with the fuel gas to provide electricity (i.e. raise high pressure steam in a boiler, pass the high pressure steam through a steam turbine to convert most of the useful energy into electricity and then use the low pressure steam to provide process heating). Furthermore, waste heat from steam condensate used in the separation section can be used to pre-heat the feed to the fermenters.

In a particularly preferred embodiment of the present invention, there is also provided, in parallel to the first fermentation step, a gasification step for the production of carbon monoxide and hydrogen from a gasifiable feedstock. Any suitable gasifiable feedstock may utilised in the gasification step, but in a preferred embodiment the gasifiable feedstock comprises non-fermentable components of the initial biomass feedstock, which components may either be separated from the biomass feedstock prior to the first fermentation step or recovered from the first fermentation step as residual solids, or a combination of both.

It has been found that ethanol may be advantageously produced from biomass feedstocks via a process in which such a gasification step is integrated with the two fermentation steps previously described.

Processes for the production of alcohols from biomass feedstocks via gasification of the feedstock to produce carbon monoxide and hydrogen, followed by fermentation into C2+ alcohols using anaerobic bacteria are known. Examples of suitable carbon monoxide fermentation processes can be found, for example, in US 2003/0211585 and US 2007/0275447, and are also described in DOE reports under DOE Contract Number DE-AC22-92PC92118, such as "Bench-scale Demonstration of Biological Production of Ethanol from Coal Synthesis Gas", Topical Report 5, November 1995.

The present invention provides a number of advantages over such known processes for the production of ethanol from biomass via gasification, especially as described in US 2003/0211585 and US 2007/0275447.

In particular, processes for production of ethanol from biomass via gasification, such as described in US 2003/0211585, tend to be net $CO_2$ producers. This $CO_2$ production may actually arise from either step of the process. Thus, the gasification step itself generally produces $CO_2$ as well as CO and $H_2$. However, in addition, although fermentation routes to higher alcohols (ethanol and heavier alcohols) from carbon monoxide may, in theory, utilise $CO_2$ as a reactant for the production of the higher alcohols, in practise the fermentation reaction also tends to be a net producer of carbon dioxide.

In particular, the bacteria used for fermentation can produce alcohols according to either of the following 2 reactions:

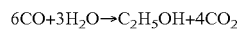
$6CO + 3H_2O \rightarrow C_2H_5OH + 4CO_2$

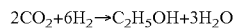
$2CO_2 + 6H_2 \rightarrow C_2H_5OH + 3H_2O$

However, the CO conversion is typically 70-90% per pass while the $H_2$ conversion is typically less than the CO conversion—therefore fermentation is also a net producer of $CO_2$.

In contrast, fermentation of biomass feedstock under conditions to convert the biomass to a product comprising acetic acid (the first fermentation step of the present invention) is a much more efficient use of the carbon content of the biomass feedstock than gasification.

However, many feedstocks cannot be fermented, but are gasifiable. Examples of such feedstocks are non-biomass feedstocks, such as plastics, and non-fermentable components of biomass feedstocks, such as lignins.

The use of both a first fermentation step and a gasification step in the process of the present invention is particularly advantageous in that it is possible to utilise efficiently a mixed waste feed whilst minimising environmental impact compared to use of gasification of such feedstocks alone and whilst being able to treat more of the feedstock than the first fermentation step alone.

Taking a general example, a mixed waste feed, after separation to remove recyclable materials such as glass, may be treated to separate a first feedstock comprising fermentable components for use as the biomass feedstock for the first fermentation step of the present invention, and a second feedstock comprising gasifiable components for use as the gasifiable feedstock for a gasification step.

Alternatively, or additionally, the gasifiable feedstock for the gasification step may comprise residual components from the first fermentation step i.e. a biomass feedstock may be subjected to the first fermentation step to produce a solution comprising acetic acid and a solid residual which solids are passed as the gasifiable feedstock for the gasification step of the present invention.

In a first aspect of this embodiment the carbon monoxide and hydrogen produced in the gasification step are passed to a further fermentation step wherein they are subjected to fermentation in the presence of an anaerobic acetogenic bacteria to produce ethanol.

The anaerobic acetogenic bacteria for this further fermentation step are not especially limited as long as they are able to convert CO and H2 into ethanol. Useful bacteria include, without limitation, those described in US 2003/0211585 and US 2007/0275447, namely *Acetogenium kivui, Acetobacterium woodii, Acetoanaerobium noterae, Clostridium aceticum, Butyribacterium methylotrophicum, Clostridium acetobutylicum, Clostridium thermoaceticum, Eubacterium limosum, Clostridium ljungdahlii* (especially strains *Clostridium ljungdahlii* PETC, *Clostridium ljungdahlii* ER12, *Clostridium ljungdahlii* C-01 and *Clostridium ljungdahlii* O-52), *Peptostreptococcus productus* and *Clostridium* carboxydivorans (especially strains P7 and P11).

Particularly preferred bacteria are *Clostridium ljungdahlii* and *Clostridium carboxydivorans*.

The conditions in the fermentation step are selected to favour ethanol production over acetic acid. As described in US 2003/211585, for example, the ratio of ethanol over acetate can be increased by manipulating the bacteria in the bioreactor, in particular by reducing the redox potential or increasing the NAD(P)H to NAD(P) ratio in the fermentation broth after said bacteria achieves a stable cell concentration in said bioreactor. This manipulation can be achieved by altering at least one parameter selected from the group consisting of nutrient medium contents, nutrient feed rate, aqueous feed rate, operating pressure, operating pH, gaseous substrate contents, gas feed rate, fermentation broth agitation rate, product inhibition step, cell density, substrate inhibition and combinations thereof. Practical examples of this are, for example, supplying an excess of H2 or a slight excess of CO or limiting the amount of calcium pantothenate in solution The process of this first aspect of the present invention results in separate product streams comprising ethanol. Preferably said ethanol product streams are combined and passed to a common ethanol treatment/separations section, avoiding unnecessary duplication of equipment.

It may be noted that the anaerobic acetogenic bacteria which are suitable for the further fermentation step of the first aspect are also anaerobic acetogenic bacteria which have been previously listed as being suitable for solventogenesis of the acetic acid and butyric acid from the first fermentation step. Thus, in a most preferred, second, aspect of this embodiment the carbon monoxide and hydrogen produced in the gasification step are passed to the second fermentation step as previously described, but in which the (solventogenic) bacteria is selected so as to be able to convert CO and H2 into ethanol.

An obvious advantage of this embodiment is that a further fermentation step is not required, the invention taking advantage of the second fermentation step previously described. Further, however, not only can the anaerobic acetogenic bacteria suitable for ethanol production from carbon monoxide and hydrogen tolerate the acetic acid from the first fermentation step, but this aspect actually results in a yet further increase in ethanol selectivity per unit of feedstock converted. In particular, it is known that the anaerobic acetogenic bacteria suitable for ethanol production from carbon monoxide and hydrogen, although highly selective for ethanol, generally also produce competing products, such as acetic acid, the production of which it is generally desired to minimise. As already described, for example, US 2003/0211585 seeks to control the conditions in the fermentation process to favour ethanol production over acetic acid, and in such a process any acetic acid formed is recycled to the fermentation step. In this aspect of the present invention acetic acid is deliberately introduced into the fermentation process (second fermentation step) with the gaseous mixture comprising carbon monoxide and hydrogen to inhibit acid formation in the second fermentation step, resulting in a net acetic acid conversion, rather than any production, in this step.

Further, the $H_2$ present in the gaseous mixture from the gasification step (b) can also be utilized to convert the acetic acid from step (a) to ethanol, giving the following equations for the conversion of the fermentable components of the initial feedstock:

$$C_6H_{12}O_6 \rightarrow 3CH_3COOH \qquad (1)$$

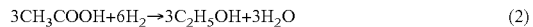
$$3CH_3COOH + 6H_2 \rightarrow 3C_2H_5OH + 3H_2O \qquad (2)$$

The net reaction for this route is:

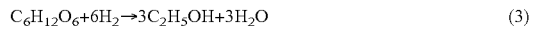
$$C_6H_{12}O_6 + 6H_2 \rightarrow 3C_2H_5OH + 3H_2O \qquad (3)$$

In effect, the presence of hydrogen results in reduced $CO_2$ and increased ethanol compared to the "conventional" overall fermentation route, which can be represented by equation (4):

$$C_6H_{12}O_6 \Longrightarrow 2C_2H_5OH + 2CO_2. \qquad (4)$$

Thus, compared to the first aspect, the second aspect of this embodiment results in a further increased ethanol selectivity per unit of feedstock converted.

Finally, the carbon monoxide present in the feedstream to the second fermentation step is a poison to many bacteria, including those present in the first fermentation step. A further advantage of this aspect therefore is that separate pasteurisation or sterilisation of the bacteria in the solution from the first fermentation may be avoided, the carbon monoxide in the second fermentation step acting to sterilise the solution in-situ in the second fermentation step. Thus, step (c)(ii) of the present invention can take place directly in the second fermentation step.

The useful bacteria for the second fermentation step in this aspect and the preferred conditions to favour ethanol production over acetic acid are as described for the first aspect. Thus, for example, useful bacteria include, without limitation, those described in US 2003/0211585 and US 2007/0275447, namely *Acetogenium kivui*, *Acetobacterium woodii*, *Acetoanaerobium noterae*, *Clostridium aceticum*, *Butyribacterium methylotrophicum*, *Clostridium acetobutylicum*, *Clostridium thermoaceticum*, *Eubacterium limosum*, *Clostridium ljungdahlii* (especially strains *Clostridium ljungdahlii* PETC, *Clostridium ljungdahlii* ER12, *Clostridium ljungdahlii* C-01 and *Clostridium ljungdahlii* O-52), *Peptostreptococcus productus* and *Clostridium* carboxydivorans (especially strains P7 and P11). Particularly preferred bacteria are *Clostridium ljungdahlii* and *Clostridium* carboxydivorans.

Compared to the processes of US 2003/0211585 and US 2007/0275447 this aspect of the present invention utilises a first fermentation step to produce a product comprising acetic acid, reducing the carbon dioxide footprint of a process using just a gasifier on the initial feedstock, and providing acetic acid which may be utilised in the second fermentation step to enhance ethanol production. This effectively results in an increased ethanol selectivity per unit of feedstock converted.

The feedstock for this embodiment of the present invention may be generally as described previously, although the ability of the gasifier to gasify feedstocks which cannot be fermented potentially widens the range of initial feedstocks which may be utilised. The pre-treatment of the feedstock may also include treatment to remove or reduce gasifiable but non-fermentable components which can then be passed to the gasification step of the present invention.

EXAMPLE

The present invention will be illustrated with respect to the following example using Municipal Solid Waste (MSW) as a biomass feedstock. The MSW is pre-treated by conventional means to make it suitable for anaerobic digestion but is not pasteurised or sterilised.

The feedstock is pre-heated and fed to a continuous fermentation vessel. The fermentation utilises a mixture of acid-producing anaerobic bacteria and the pH of the fermentation is maintained at less than pH 6 to inhibit methanogenesis. The temperature is maintained at about 55° C., which increases the rate of acid production and selectivity to acetic acid rather than higher carboxylic acids, and also helps to inhibit methanogenesis.

Fermented broth containing 2 to 5 wt % acetic acid, 0.2 to 1 wt % butyric acid and small amounts of other carboxylic acids is removed and filtered to remove residual solids. The broth is pasteurised by heating to 72° C. The broth is then passed to a second fermentation vessel. This second fermentation utilises the bacteria *Clostridium acetobutylicum* to convert the carboxylic acids to the relevant alcohols of the same number of carbon atoms.

The product from this step contains 2 to 5 wt % ethanol, 0.2 to 1 wt % butanol and smaller amounts of other alcohols, and is filtered to remove any solids and bacteria. The filtrate is then heated and fed to a distillation column. The distillation bottom product, containing mostly water with small amounts of C5 and above carboxylic acids and solvents, is used to pre-heat the column feed and then recycled to the primary fermentation vessel. To avoid a build up of contaminants in the first fermentation step a small liquid purge may be taken from any suitable point in the process.

A liquid product containing about 40 wt % butanol, along with water, ethanol, propanol and pentanol, is removed as a side draw from the distillation column.

A liquid product containing about 94 wt % ethanol is removed from just below the top of the distillation column. (The liquid product is taken from a number of stages down from the top of the column to allow the removal of light components, including methane, CO2, hydrogen, etc. as a top vapour product from the column.)

The ethanol liquid product is further dehydrated by being contacted with a molecular sieve to give a product >99 wt % ethanol for use as a fuel or chemical feedstock.

The invention claimed is:

1. A process for the production of ethanol and butanol using two separate fermentation steps comprising:
   a) first fermentation step comprising fermenting feedstock; wherein subjecting said feedstock to anaerobic fermentation in the presence of acetogenic bacteria, further comprising a mixture of bacterial strains, at a pH below 6.0, at a temperature in the range 20 to 70 degree C, converting said feedstock to a product predominantly comprising acetic acid and butyric acid; wherein ratio of acetic acid to butyric acid is at least 2:1;
   b) treating said product predominantly comprising acetic acid and butyric acid of step a) to separate a solution comprising the acetic acid and butyric acid by:
      (i) separating residual solids; and
      (ii) separating bacteria; optionally pasteurizing; optionally sterilising said solution comprising the acetic acid and butyric acid;
   c) second fermentation step comprising fermenting in the presence of solventogenic bacteria said solution comprising the acetic acid and butyric acid from step b) to form ethanol and butanol.

2. A process according to claim 1 wherein said product predominantly comprising acetic acid and butyric acid from step a) has a concentration of acetic acid in solution of 2 to 5 wt % and a concentration of butyric acid in solution of 0.2 to 0.75 wt %.

3. A process according to claim 2 wherein said products ethanol and butanol from step c) comprises ethanol at a concentration of ethanol in solution in the range 2 to 5 wt % and butanol at a concentration of butanol in solution in the range 0.2 to 0.75 wt %.

4. The process of claim 1, wherein step a) uses a mixture of bacterial strains; including at least some of the bacteria present in the feedstock.

5. The process of claim 1, wherein the pH in step a) is maintained in the range 3.0 to 5.5.

6. The process of claim 1, wherein the temperature in step a) is the range 40 to 70 degree C.

7. The process of claim 1, wherein the conditions in said first fermentation step are such that the acetic acid and butyric acid in said product predominantly comprising acetic acid and butyric acid from step a) are present in a combined concentration of at least 60 wt % of the total weight of carboxylic acids.

8. A process according to claim 1 wherein said product predominantly comprising acetic acid and butyric acid from step a) comprises at least a 4:1 weight ratio of acetic acid to butyric acid and a combined concentration of the acetic acid and butyric acid of at least 90 wt % of the total weight of carboxylic acids.

9. The process of claim 1, wherein step b) comprises filtration to remove any residual solids.

10. The process of claim 1, wherein step b) comprises pasteurisation or sterilisation of the solution.

11. The process of claim 1, wherein step c) uses a solventogenic bacteria selected from *Acetogenium kivui, Acetobacterium woodii, Acetoanaerobium noterae, Clostridium aceticum, Butyribacterium methylotrophicum, Clostridium acetobutylicum, Clostridium thermoaceticum, Eubacterium limosum, Clostridium ljungdahlii, Peptostreptococcus productus, Clostridium carboxydivorans, Clostridium beijerinkii, Clostridium aurantibutyricum*, and *Clostridium tetanomorphum*.

12. The process of claim 1, wherein said biomass feedstock is landfill leachate.

13. A process according to claim 1 wherein the said solventogenic bacteria in step c) are selected *Acetogenium kivui, Acetobacterium woodii, Acetoanaerobium noterae, Clostridium aceticum, Butyribacterium methylotrophicum, Clostridium acetobutylicum, Clostridium thermoaceticum, Eubacterium limosum, Clostridium ljungdahlii, Peptostreptococcus productus* and *Clostridium carboxydivorans*.

14. A process according to claim 1 wherein said solventogenic bacteria in step c) is selected from *Clostridium ljungdahlii* and *Clostridium carboxydivorans*.

* * * * *